(12) United States Patent
Molenda et al.

(10) Patent No.: US 8,758,453 B2
(45) Date of Patent: Jun. 24, 2014

(54) PROCESS FOR TREATING HAIR

(75) Inventors: Michael Molenda, Frankfurt (DE); Sandra Schmelz, Marktheidenfeld (DE)

(73) Assignee: Kao Germany GmbH, Darmstadt (DE)

( * ) Notice: Subject to any disclaimer, the term of this patent is extended or adjusted under 35 U.S.C. 154(b) by 0 days.

(21) Appl. No.: 14/124,411

(22) PCT Filed: May 22, 2012

(86) PCT No.: PCT/EP2012/059432
§ 371 (c)(1),
(2), (4) Date: Dec. 6, 2013

(87) PCT Pub. No.: WO2012/168062
PCT Pub. Date: Dec. 13, 2012

(65) Prior Publication Data
US 2014/0123405 A1 May 8, 2014

(30) Foreign Application Priority Data

Jun. 10, 2011 (EP) .................................. 11169433

(51) Int. Cl.
*A61Q 5/10* (2006.01)
*A61K 8/44* (2006.01)

(52) U.S. Cl.
CPC .. *A61K 8/442* (2013.01); *A61Q 5/10* (2013.01)
USPC ................ 8/405; 8/406; 8/408; 8/485; 8/580; 132/202; 132/208

(58) Field of Classification Search
USPC .............. 8/405, 406, 408, 485, 580; 132/202, 132/208
See application file for complete search history.

(56) References Cited

U.S. PATENT DOCUMENTS 7,232,466 B2 * 6/2007 Narasimhan et al. ............. 8/405

* cited by examiner

*Primary Examiner* — Eisa Elhilo
(74) *Attorney, Agent, or Firm* — Norris McLaughlin & Marcus P.A.

(57) ABSTRACT

Present invention relates to a process for treating hair for achieving better oxidative coloration with improved durability and improved hair conditioning. Accordingly, the first object of the present invention is a process for treating hair comprising the steps wherein hair is dyed with a composition comprising one or more hair dye and at least one oxidizing agent wherein the composition is obtained by mixing two compositions wherein the first composition, composition A, comprises one or more hair dye and the second composition, Composition B, comprises at least one oxidizing agent, and in a further step hair is treated with a composition (Composition C) comprising at least one surfactant other than amino acid surfactant with the condition that at least two of the compositions A, B and C comprise at least one amino acid surfactant and composition C is substantially free from sulphate surfactants.

14 Claims, No Drawings

PROCESS FOR TREATING HAIR

This application is a 371 application of PCT/EP2012/059432 filed May 22, 2012, which claims foreign priority benefit under 35 U.S.C. §119 of European Application No. 11169433.7 filed Jun. 10, 2011.

Present invention relates to a process for treating hair for intensive oxidative colouring with better durability and improved hair conditioning.

Oxidative dyeing hair has been commonly used for obtaining durable colours for many years. Problems encountered with the oxidative dyeing have been addressed in various patent and non-patent literatures. Colour durability is, on one hand, dependent on the dyestuffs used, but, on the other hand, any additional cosmetic composition and especially cleansing composition used after colouring hair plays an important role in determining the durability of the colour.

The aim of the present invention is to find out optimal process for treating hair for securing intensive coloration with optimal durability and with improved hair conditioning, especially of hair with parts having different degree of damage. It is often the case that the parts having no or negligible level of damage allow colouring quite well without any problem, but the parts with considerable level of damage, due to environmental influences or previous chemical treatments especially of reductive and/or oxidative steps, do not present the same colour properties. This leads to the problems of colour inhomogenity both immediately after colouring and, especially importantly, after several wash cycles because of variable durability characteristics of the colours depending on hair damage level.

The inventors of the present invention have surprisingly found out that hair treated with the process of the present invention has excellent cosmetic properties and colours so obtained are intensive and have improved homogeneity during the whole lifecycle.

Accordingly, the first object of the present invention is a process for treating hair comprising the steps wherein hair is dyed with a composition comprising one or more hair dye and at least one oxidizing agent wherein the composition is obtained by mixing two compositions prior to application onto hair wherein the first composition, composition A, comprises one or more hair dye and the second composition, Composition B, comprises at least one oxidizing agent, and in a further step hair is treated with a composition (Composition C) comprising at least one surfactant other than amino acid surfactant with the condition that at least two of the compositions A, B and C comprise at least one amino acid surfactant and composition C is substantially free of sulphate surfactants.

Second object of the present invention is a kit for treating hair comprising at least three compositions wherein the first composition, Composition A, comprises one or more hair dye, the second composition, Composition B, comprises at least one oxidizing agent and the third composition, Composition C, comprises at least one surfactant other than amino acid surfactant, with the condition that at least two of the compositions, Compositions A, B and C, comprise at least one amino acid surfactant and composition C is substantially free of sulphate surfactant.

The third object of the present invention is the use of the process of the present invention for colouring hair, especially for achieving homogeneous and durable colours on hair, especially on damaged hair.

Composition A comprises one or more hair dye selected from direct and oxidative dyes. Direct dyes are preferably selected from the anionic and/or cationic and/or neutral nitro dyes. It should be noted that the composition A may certainly comprise the mixture of cationic, anionic and neutral nitro dyes in addition to an oxidative hair dye.

Any cationic direct dye is in principal suitable for the composition A. Non-limiting preferred examples are Basic Blue 6, Basic Blue 7, Basic Blue 9, Basic Blue 26, Basic Blue 41, Basic Blue 99, Basic Brown 4, Basic Brown 16, Basic Brown 17, Natural Brown 7, Basic Green 1, Basic Orange 31, Basic Red 2, Basic Red 12 Basic Red 22, Basic Red 51, Basic Red 76, Basic Violet 1, Basic Violet 2, Basic Violet 3, Basic Violet 10, Basic Violet 14, Basic Yellow 57 and Basic Yellow 87, and mixtures thereof.

Any anionic dye is in principal suitable for the composition A. Suitable non-limiting examples are Acid Black 1, Acid Blue 1, Acid Blue 3, Food Blue 5, Acid Blue 7, Acid Blue 9, Acid Blue 74, Acid Orange 3, Acid Orange 6, Acid Orange 7, Acid Orange 10, Acid Red 1, Acid Red 14, Acid Red 18, Acid Red 27, Acid Red 50, Acid Red 52, Acid Red 73, Acid Red 87, Acid Red 88, Acid Red 92, Acid Red 155, Acid Red 180, Acid Violet 9, Acid Violet 43, Acid Violet 49, Acid Yellow 1, Acid Yellow 23, Acid Yellow 3, Food Yellow No. 8, D&C Brown No. 1, D&C Green No. 5, D&C Green No. 8, D&C Orange No. 4, D&C Orange No. 10, D&C Orange No. 11, D&C Red No. 21, D&C Red No. 27, D&C Red No. 33, D&C Violet 2, D&C Yellow No. 7, D&C Yellow No. 8, D&C Yellow No. 10, FD&C Red 2, FD&C Red 40, FD&C Red No. 4, FD&C Yellow No. 6, FD&C Blue 1, Food Black 1, Food Black 2, Disperse Black 9 and Disperse Violet 1 and their alkali metal salts such as sodium, potassium, and mixtures thereof. Among those, the preferred anionic dyestuffs are Acid Red 52, Acid Violet 2, Acid Red 33, Acid Orange 4, Acid Red 27, Acid Blue 9 and Acid Yellow 10 and their salts, and mixtures thereof. The most preferred anionic dyes are Acid Red 52, Acid Violet 2, Acid Red 33, Acid Blue 9, Acid Orange 4 and Acid Yellow 10, and their salts, and mixtures thereof.

Any neutral nitro dye is in principal suitable for the composition A. Suitable non-limiting examples are HC Blue No. 2, HC Blue No. 4, HC Blue No. 5, HC Blue No. 6, HC Blue No. 7, HC Blue No. 8, HC Blue No. 9, HC Blue No. 10, HC Blue No. 11, HC Blue No. 12, HC Blue No. 13, HC Brown No. 1, HC Brown No. 2, HC Green No. 1, HC Orange No. 1, HC Orange No. 2, HC Orange No. 3, HC Orange No. 5, HC Red BN, HC Red No. 1, HC Red No. 3, HC Red No. 7, HC Red No. 8, HC Red No. 9, HC Red No. 10, HC Red No. 11, HC Red No. 13, HC Red No. 54, HC Red No. 14, HC Violet BS, HC Violet No. 1, HC Violet No. 2, HC Yellow No. 2, HC Yellow No. 4, HC Yellow No. 5, HC Yellow No. 6, HC Yellow No. 7, HC Yellow No. 8, HC Yellow No. 9, HC Yellow No. 10, HC Yellow No. 11, HC Yellow No. 12, HC Yellow No. 13, HC Yellow No. 14, HC Yellow No. 15, 2-Amino-6-chloro-4-nitrophenol, picramic acid, 1,2-Diamino-4-nitrobenzol, 1,4-Diamino-2-nitrobenzol, 3-Nitro-4-aminophenol, 1-Hydroxy-2-amino-3-nitrobenzol and 2-hydroxyethylpicramic acid, and mixtures thereof.

Total concentration of direct dyes is in the range of 0.001 to 10% by weight, preferably 0.01 to 7.5% more preferably 0.05 to 5% and most preferably 0.1 to 5% by weight calculated to total of the composition A. The most preferred among the direct dyes is cationic direct dyes.

In principal all oxidative dye precursors available for hair colouring purposes are suitable within the meaning of the present invention in Composition A. Special mention is made of p-phenylenediamine, p-aminophenol and substituted p-phenylenediamines such as 2,5-diamino-toluene, 2-n-propyl or 2-ethyl-p-phenylenediamine, 2,6-di-methyl-p-phenylene-diamine, 2-(2,5-diaminophenyl) ethanol, 1-amino-4-bis-(2'-hydroxy-ethyl)amino-benzene, 2-(2-hydroxyethyl amino)-5-aminotoluene, 4,4'-diaminodiphenylamine, 4-aminodiphenylamine, 2-amino-5-N,N-diethyl aminotoluene, 4-amino-N-ethyl-N-isopropyl aniline, 2-chloro-p-phenylenediamine, 1-β-hydroxyethyl-2,5-diamino-4-chlorobenzene, 1-β-hydroxyethyl-2,5-diamino-4-methyl benzene, 2-methoxy-p-phenylenediamine, N,N-diethyl-p-phenylenediamine, 1-amino-4-β-methoxyethyl aminobenzene, 1-dimethyl-amino-4-aminobenzene, 1-hydroxy-2,5-diamino-4-methyl benzene, 1-hydroxymethyl-2,5-diaminobenzene, 1,3-dimethyl-2,5-diaminobenzene, 1,4-diamino isopropyl benzene and/or 1-amino-4-β-hydroxypropyl aminobenzene, pyrazole and the derivatives thereof such as 1-hydroxyethyl-4,5-diaminopyrazole, 3,4-diamino-5-hydroxypyrazole, 3,5-diaminopyrazole, 3,5-diamino pyrazol-1-carboxamide, 3-amino-5-hydroxypyrazole, 1-phenyl-2-methylpyrazole, 1-phenyl-3-methylpyrazole-5-one, 3,5-dimethylpyrazole, 3,5-dimethylpyrazole-1-methanol, 3,5-diamino-1,2,4-triazole, 4-aminophenol and the derivatives thereof such as 4-amino-3-methylphenol, 2-chloro-4-aminophenol, 2,6-dichloro-4-aminophenol, 2,4-diamino-phenol, 2,6-dibromo-4-aminophenol, tetramino pyrimidines, triaminohydroxy pyrimidines, diaminomono- and -dihydroxy pyrimidines, aminotriazines, 5-amino salicylic acid and/or 1,2,4-triamino benzene or the water-soluble salts thereof.

Further suitable ones aminopyridines are 2,5-diaminopyridine, 2,3-diaminopyridine, 2,6-diaminopyridine, 3-amino-2-methyl amino-6-methoxypyridine, 2-dimethyl-5-aminopyridine, 2-dimethyl aminoethyl-3-hydroxypyridine, 2-amino-4,6-dimethylpyridine, 2-amino-3-hydroxypyridine, 3-amino-2(β-hydroxyethyl amino)-6-methoxy-pyridine, 2,6-dimethyl amino-5-aminopyridine, 2-di(hydroxyethyl)amino-5-aminopyridine, 2-hydroxyethyl amino-5-aminopyridine, 4-hydroxy-2,5,6-triaminopyrimidine and/or the water-soluble salts thereof.

Within the meaning of the present invention above mentioned developers can as well be present as a mixture with each other.

The total concentration of the oxidative dye precursors also called as developing substances customarily ranges between 0.001 to 5%, preferably 0.01 to 4% and more preferably 0.05 to 3%, and most preferably 0.1 to 2% by weight, calculated to the total of the composition A In a further embodiment of the present invention compositions comprise in addition to at least one oxidative dye precursor at least one coupling substance. As a rule any coupling substance customarily used in oxidative hair colouration area is suitable within the meaning of the present invention. Non-limiting coupling substances, are 5-amino-2-methylphenol, 2-methyl-5-hydroxyethylaminophenol, 2,4,-diamnophenoxyehanol, 2-amino-4-hydroxyethylaminoanisol, 2-methyl-5-amino-6-chlorphenol, 1,3-bis(2,4-diaminophenoxy)propane, 2-bis(2-hydroxyethyl)aminotoluene, 2-amino-5-methylphenol, resorcinol, 2-methyl-resorcinol, 4-chlororesorcinol, 2-amino-4-chlorophenol, 5-amino-4-methoxy-2-methylphenol, 2-aminophenol, 3-amino-phenol, 1-methyl-2-hydroxy-4-aminobenzene, 3-N,N-dimethyl aminophenol, 2,6-dihydroxy-3,5-dimethoxypyridine, 5-amino-3-methylphenol, 6-amino-3-methylphenol, 1,3-diamino-benzene, 1-amino-3-(2'-hy-droxyethylamino)benzene, 1-amino-3-[bis(2'-hydroxy-ethyl)amino]benzene, α-naphthol, 4,6-dichlororesorcinol, 1,3-diamino-toluene, 4-hydroxy-1,2-methylenedioxy benzene, 1,5-dihydroxy naphthalene, 1,6-dihydroxy naphthalene, 1,7-dihydroxy naphthalene, 2,7-dihydroxy naphthalene, 1-hydroxy-2-methyl naphthalene, 4-hydroxy-1,2-methyldioxy benzene, 2,4-diamino-3-chlorophenol, 5-amino-2-methoxyphenol and/or 1-methoxy-2-amino-4-(2'-hydroxyethyl amino)benzene and/or 1,3-bis(2,4-diaminophenoxy) propane or the water-soluble salts thereof. One or more of the above mentioned coupler can also be used in a mixture.

In the composition A, the coupling substance(s) as reaction partners of the developing substance(s) are present in approximately the same molecular proportions as the developing substances, i.e. in amounts from 0.001 to 5%, preferably 0.01 to 4% and more preferably 0.05 to 3%, and most preferably 0.1 to 2% by weight, calculated to the total of the Composition A.

Composition A has a pH between 6 and 12, preferably 6.5 and 11 and more preferably 6.8 and 10.5 and comprises at least one alkalizing agent.

Composition A of the present invention comprises preferably at least one alkalizing agent, preferably selected from ammonia (or ammonium hydroxide) and a compound according to the following general structure

$R_4R_5R_6N$ wherein $R_4$, $R_5$ and $R_6$ are same or different H, $C_1$-$C_6$ alkyl, $C_1$-$C_6$ monohydroxyalkyl or $C_2$-$C_6$ polyhydroxyalkyl with the condition that at least one of $R_4$, $R_5$ and $R_6$ is a mono or polyhydroxyalkyl and their mixtures. In the preferred embodiment of the present invention, at least one alkanolamine is selected from compounds according to the above general structure wherein $R_4$, $R_5$ and $R_6$ are same or different H, $C_1$-$C_4$ alkyl, $C_1$-$C_4$ monohydroxyalkyl or $C_2$-$C_4$ polyhydroxyalkyl with the condition that at least one of $R_4$, $R_5$ and $R_6$ is a mono or polyhydroxyalkyl.

According to the most preferred embodiment of the present invention at least one alkanolamine is selected from compounds according to the above general formula wherein $R_4$, $R_5$ and $R_6$ are same or different H, $C_2$-$C_4$ alkyl, $C_2$-$C_4$ monohydroxyalkyl or $C_2$-$C_4$ polyhydroxyalkyl with the condition that at least one of $R_4$, $R_5$ and $R_6$ is a mono or polyhydroxyalkyl. Suitable alkanolamines according to the general formula of above are monoethanolamine, diethanolamine, triethanolamine, monoethanol methylamine, monoethanoldimethylamine, di-ethanol/methylamine, monoethanolethylamine, monoethanoldiethylamine, diethanolethylamine, monoethanolpropylamine, monoethanoldipropylamine, diethanolpropylamine, monoethanolbutylamine and diethanolbutylamine. Preferred are monoethanolamine, diethanolamine and triethanolamine. The most preferred alkanolamine is monoethanolamine.

The total concentration of alkalizing agent in the compositions varies between 1 and 35%, preferably 1 and 30%, more preferably 2.5 and 25% and most preferably 2.5 to 20% by weight calculated to the total of the composition A.

Composition B of the present invention comprises at least one oxidizing agent. Suitable oxidizing agents are hydrogen peroxide, urea peroxide, melamin peroxide or perborate salts. The most preferred is hydrogen peroxide. Concentration of at least one oxidizing agent is in the range of 0.1 to 20%, preferably 0.2 to 15%, more preferably 0.5 to 15% and most preferably 1 to 12% by weight, calculated to total of the composition B.

pH of the composition B is acidic and therefore comprises at least one acidic compound selected form organic acids such as citric acid, lactic acid, malic and maleic acids, and inorganic acids such as phosphoric acid.

Composition C is preferably a cleansing composition and comprises one or more surfactants selected from anionic, non-ionic and amphoteric surfactants other than amino acid surfactant and it is free of sulphate surfactants. Total surfactant concentration is in the range of 5 to 35%, preferably 5 to 30%, more preferably 10 to 25% and most preferably 10 to 20% by weight, calculated to the total of the composition C.

In the preferred embodiment of the present invention composition C comprises at least one anionic surfactant, at least one non-ionic surfactant and at least one amphoteric surfactant other than amino acid surfactant.

Suitable anionic surfactants of the carboxylate type are alkyl polyether carboxylic acids and the salts thereof of the formula

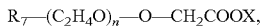

wherein $R_7$ is a $C_8$-$C_{20}$-alkyl group, preferably a $C_{12}$-$C_{14}$-alkyl group, n is a number from 1 to 20, preferably 2 to 17, and X is H or preferably a cation of the group sodium, potassium, magnesium and ammonium, which can optionally be hydroxyalkyl-substituted, as well as alkyl amido polyether carboxylic acids of the general formula

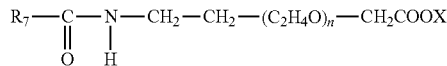

wherein $R_7$ and X have the above meanings, and n is in particular a number from 1 to 10, preferably 2.5 to 5.

Such products have been known for some time and are on the market, for example, under the trade name "AKYPO®" and "AKYPO-SOFT®".

Nonionic surfactants preferred in the cleansing composition according to the invention are alkyl polyglucosides of the general formula

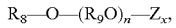

wherein $R_8$ is an alkyl group with 8 to 18 carbon atoms, $R_9$ is an ethylene or propylene group, Z is a saccharide group with 5 to 6 carbon atoms, n is a number from 0 to 10 and x is a number between 1 and 5. Especially suited examples are decyl polyglucoside, cocoyl polyglucoside and lauryl polyglucoside.

Further nonionic surfactants are long-chain fatty acid dialkanolamides, such as coco fatty acid diethanolamide and myristic fatty acid diethanolamide.

Further additionally useful nonionic surfactants are, for example, the various sorbitan esters, such as polyethylene glycol sorbitan stearic acid ester, fatty acid polyglycol esters or poly-condensates of ethyleneoxide and propyleneoxide, as they are on the market, for example, under the trade name "Pluronics®", as well as fatty alcohol ethoxylates.

Further suitable nonionic surfactants are aminoxides. Such aminoxides are state of the art, for example $C_{12}$-$C_{18}$-alkyl dimethyl aminoxides such as lauryl dimethyl aminoxide, $C_{12}$-$C_{18}$-alkyl amidopropyl or -ethyl aminoxides, $C_{12}$-$C_{18}$-alkyl di(hydroxyethyl) or (hydroxypropyl)aminoxides, or also aminoxides with ethyleneoxide and/or propyleneoxide groups in the alkyl chain. Such aminoxides are on the market, for example, under the trade names "Ammonyx®", "Aromox®" or "Genaminox®".

Further nonionic surfactants useful in the compositions according to invention are $C_{10}$-$C_{22}$-fatty alcohol ethoxylate. Especially suited are $C_{10}$-$C_{22}$-fatty alcohol ethers, the alkyl polyglycol ethers known by the generic terms "Laureth", "Myristeth", "Oleth", "Ceteth", "Deceth", "Steareth" and "Ceteareth" according to the CTFA nomenclature, including addition of the number of ethylene oxide molecules, e.g., "Laureth-16":

The average degree of ethoxylation thereby ranges between about 2.5 and about 25, preferably about 10 and about 20.

The more preferred non-ionic surfactants are alkyl polyglucosides such as decyl, cocoyl polyglucoside and ethoxylated fatty alcohols such as laureth-16. Especially preferred are alkyl polyglucosides such as decyl, cocoyl polyglucoside.

Suitable amphoteric surfactants are betaines such as alkyl betaines, fatty acid amidoalkyl betaines, long-chain alkyl amino acids, such as cocoaminoacetate, cocoaminopropionate and sodium cocoamphopropionate and -acetate have also proven suitable.

In detail, suitable betaine surfactants are of general structure

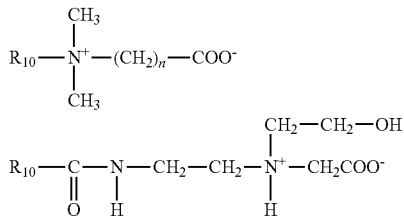

wherein $R_{10}$ is a $C_8$-$C_{18}$-alkyl group and n is 1 to 3; and amidoalkyl betaines of the structure

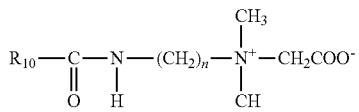

wherein $R_{10}$ and n are same as above.

The most preferred amphoteric surfactants are alkyl betaines such as lauryl betaine and alkyl amido betaines such as cocamidopropyl betaine.

At least two of the compositions A, B and C comprise at least one amino acid surfactant. Preferably at least one amino acid surfactant is an anionic surfactant and selected from the ones according to the general structure

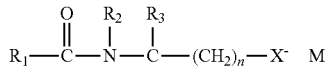

wherein $R_1$ is a saturated or unsaturated, straight or branched alkyl chain with 7 to 17 C atoms, $R_2$ is H or a methyl, $R_3$ is H, $COO^-M^+$, $CH_2COO^-M$ or $COOH$, n is 0 to 2, X is $COO^-$ and M is independent from each other H, sodium, potassium or ammonium.

With the term amino acid surfactants especially those surfactants are meant derived from glutamate, alanin or alaninate, sarcosinate and aspartate. Preferred are glutamate and sarcosinate surfactants and mixtures thereof.

Suitable glutamate surfactants which are at the same time especially preferred are according to the general formula

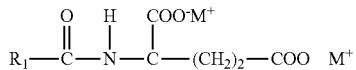

wherein $R_1$ is preferably a saturated or unsaturated, straight or branched alkyl chain with 7 to 17 C atoms, and more preferably 9 to 13 C atoms, and M is independent from each other H, ammonium, sodium or potassium. Suitable examples are dipotassium capryloyl glutamate, dipotassium undecylenoyl glutamate, disodium capryloyl glutamate, disodium cocoyl glutamate, disodium lauroyl glutamate, disodium stearoyl glutamate, disodium undecylenoyl glutamate, potassium capryloyl glutamate, potassium cocoyl glutamate, potassium lauroyl glutamate, potassium myristoyl glutamate, potassium stearoyl glutamate, potassium undecylenoyl glutamate, sodium capryloyl glutamate, sodium cocoyl glutamate, sodium lauroyl glutamate, sodium myristoyl glutamate, sodium olivoyl glutamate, sodium palmitoyl glutamate, sodium stearoyl glutamate, and sodium undecylenoyl glutamate and mixtures thereof. Preferred are disodium capryloyl glutamate, disodium cocoyl glutamate, disodium lauroyl glutamate, potassium capryloyl glutamate, potassium cocoyl glutamate, potassium lauroyl glutamate, potassium myristoyl glutamate, sodium capryloyl glutamate, sodium cocoyl glutamate, sodium lauroyl glutamate, and sodium myristoyl glutamate and mixtures thereof. More preferred are disodium capryloyl glutamate, disodium cocoyl glutamate, disodium lauroyl glutamate, potassium capryloyl glutamate, potassium cocoyl glutamate, potassium lauroyl glutamate, sodium capryloyl glutamate, sodium cocoyl glutamate, and sodium lauroyl glutamate and mixtures thereof. Sodium cocoyl glutamate and/or Sodium lauroyl glutamate is especially preferred.

Suitable alanine or alaninate surfactants are according to the general formula

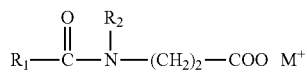

wherein $R_1$ is preferably a saturated or unsaturated, straight or branched alkyl chain with 7 to 17 C atoms, and more preferably 9 to 13 C atoms, $R_2$ is H or methyl and M is H, sodium or potassium. Suitable examples are cocoyl methyl β-alanine, lauroyl β-alanine, lauroyl methyl β-alanine, myristoyl β-alanine, potassium lauroyl methyl β-alanine, sodium cocoyl alaninate, sodium cocoyl methyl β-alanine and sodium myristoyl methyl β-alanine and mixtures thereof.

Suitable glycine surfactants are according to the general formula

wherein $R_1$ is preferably a saturated or unsaturated, straight or branched alkyl chain with 7 to 17 C atoms, and more preferably 9 to 13 C atoms, and M is H, sodium or potassium. Suitable examples are palmitoyl glycine, sodium lauroyl glycine, sodium cocoyl glycine, sodium myristoyl glycine, potassium lauroyl glycine, and potassium cocoyl glycine and mixtures thereof.

Suitable sarcosinate surfactants are according to the general formula

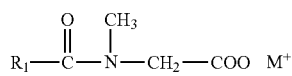

wherein $R_1$ is preferably a saturated or unsaturated, straight or branched alkyl chain with 7 to 17 C atoms, and more preferably 9 to 13 C atoms, and M is H, sodium or potassium. Suitable examples are potassium lauroyl sarcosinate, potassium cocoyl sarcosinate, sodium cocoyl sarcosinate, sodium lauroyl sarcosinate, sodium myristoyl sarcosinate, and sodium palmitoyl sarcosinate and mixtures thereof. Preferred are potassium lauroyl sarcosinate, potassium cocoyl sarcosinate, sodium cocoyl sarcosinate, and sodium lauroyl sarcosinate and mixtures thereof. More preferred are sodium cocoyl sarcosinate, and sodium lauroyl sarcosinate and mixtures thereof.

Suitable aspartate surfactants are according to the general formula

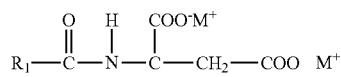

wherein $R_1$ is preferably a saturated or unsaturated, straight or branched alkyl chain with 7 to 17 C atoms, and more preferably 9 to 13 C atoms, and M is independent from each other H, sodium or potassium. Suitable examples are sodium lauroyl aspartate, sodium myristoyl aspartate, sodium cocoyl aspartate, sodium caproyl aspartate, disodium lauroyl aspartate, disodium myristoyl aspartate, disodium cocoyl aspartate, disodium caproyl aspartate, potassium lauroyl aspartate, potassium myristoyl aspartate, potassium cocoyl aspartate, potassium caproyl aspartate, dipotassium lauroyl aspartate, dipotassium myristoyl aspartate, dipotassium cocoyl aspartate, and dipotassium caproyl aspartate and mixtures thereof. Preferred are sodium lauroyl aspartate, sodium myristoyl aspartate, sodium cocoyl aspartate, and sodium caproyl aspartate and mixtures thereof.

It should be noted that compositions of the present invention can also comprise mixture of several type of amino acid surfactants such as mixture of glutamate and sarcosinate surfactants.

Concentration of at least one amino acid surfactant in the compositions of the present invention is in the range of 0.1 to 15%, preferably 0.5 to 12.5% and more preferably 0.5 to 10% and most preferably 1 to 10% by weight calculated to total of each composition.

In a preferred embodiment of the present invention all of the three compositions A, B and C comprise at least one amino acid surfactant.

One or more of the compositions A, B and C preferably comprises at least one natural oil. In the more preferred embodiment at least two of the compositions A, B and C and most preferably all three compositions comprise at least one natural oil. Suitable non-limiting examples are argan oil, shea butter oil, karite oil, olive oil, almond oil, avocado oil, ricinus oil, coconut oil, palm oil, sesame oil, peanut oil, sunflower oil, peach kernel oil, wheat germ oil, macadamia nut oil, macadamia oil, night primrose oil, jojoba oil, castor oil, soya oil, lanolin, passiflora oil, black cumin oil, borage oils, grapeseed oil, hempseed oil, kukui nut oil, and rosehip oil. Preferred are argan oil, shea butter oil, karite oil, olive oil, almond oil, avocado oil, ricinus oil, coconut oil, palm oil, sesame oil, peanut oil, whale oil, sunflower oil, peach kernel oil, wheat germ oil, macadamia nut oil, macadamia oil, night primrose oil, jojoba oil, castor oil, and soya oil. More preferred are argan oil, shea butter oil, karite oil, macadamia nut oil, macadamia oil, olive oil, almond oil, avocado oil, ricinus oil, coconut oil, palm oil, sesame oil, peanut oil, sunflower oil, peach kernel oil, wheatgerm oil, jojoba oil, castor oil, and soya oil. Most preferred are argan oil, shea butter oil, karite oil, olive oil, almond oil, avocado oil, coconut oil, macadamia nut oil, macadamia oil, palm oil, sesame oil, peach kernel oil, wheatgerm oil, jojoba oil, and soya oil. Particularly preferred are argan oil, shea butter oil and karite oil which may be comprised as a single oil component or in admixture with each other.

Concentration of at least one natural oil is in the range of 0.01 to 5%, preferably 0.02 to 4%, more preferably 0.05 to 2.5% and most preferably 0.1 to 1.5% by weight calculated to total of each composition.

One or more of the compositions A, B and C preferably comprises at least one cationic surfactant according to the formula,

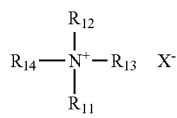

where $R_{12}$ is a saturated or unsaturated, branched or non-branched alkyl chain with 8-22 C atoms or

where $R_{15}$ is saturated or unsaturated, branched or non-branched alkyl chain with 7-21 C atoms and n has typical value of 1-4 or

where $R_{16}$ is saturated or unsaturated, branched or non-branched alkyl chain with 7-21 C atoms and n has typical value of 1-4, and $R_{11}$ is unsaturated or saturated, branched or non-branched alkyl chain with 1-22 C atoms or

or

where $R_{15}$, $R_{16}$ and n are same as above.

$R_{13}$ and $R_{14}$ are lower alkyl chain with 1 to 4 Carbon atoms, and X is typically chloride, bromide, methosulfate.

Typical examples of those ingredients are cetyl trimethly ammonium chloride, stear trimonium chloride, dipalmitoyl dimonium chloride, distearyl dimethyl ammonium chloride, stearamidopropyl trimonuim chloride, dioleoylethyl dimethyl ammonium methosulfate, dioleoylethyl hydroxyethylmonium methosulfate.

Cationic surfactant concentration is in the range of 0.1 to 5%, preferably 0.2 to 4%, more preferably 0.2 to 3% and most preferably 0.25 to 2.5% by weight calculated to total of each composition.

Composition of the present invention comprises preferably at least one fatty alcohol or mixture of fatty alcohols with the chain length of 14 to 22 C atoms which may be straight or branched, saturated or unsaturated. Non-limiting examples to suitable fatty alcohols are myristyl alcohol, cetyl alcohol, stearyl alcohol, behenyl alcohol, oleyl alcohol and cetostearyl alcohol, octyldodecanol. The most preferred is cetostearyl alcohol well known with its trade name Lanette O from Cognis. Total fatty alcohol concentration is in the range of 0.1 to 20%, preferably 0.2 and 15%, more preferably 0.5 and 10% and most preferably 0.5 to 7.5% by weight, calculated to total of each composition.

In a further preferred embodiment, compositions A, B or C of the present invention comprises additional compounds such as oily substances, non-ionic substances and cationic polymers.

Oily substances are selected from such as silicone oils, either volatile or non-volatile, and synthetic oils. Among silicone oils those can be added to the compositions include dimethicone, dimethiconol, polydimethylsiloxane, DC fluid ranges from Dow Corning, arylated silicones such as phenyl trimethicone or any other silicone with up to 5 aryl, preferably phenyl, group in its molecule such as trimethyl pentaphenyl trisiloxane, and the synthetic oils, such as mineral oil, isopropyl myristate, palmitate, stearate and isostearate, oleyl oleate, isocetyl stearate, hexyl laurate, dibutyl adipate, dioctyl adipate, myristyl myristate and oleyl erucate.

Non-ionic conditioning agents can be polyols such as glycerin, glycol and derivatives, polyethyleneglycoles known with trade names Carbowax PEG from Union Carbide and Polyox WSR range from Amerchol, polyglycerin, polyethyleneglycol mono or di fatty acid esters having general formula

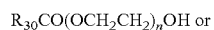

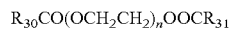

where $R_{30}$ and $R_{31}$ are independent from each other saturated, unsaturated or branched or non-branched alkyl chain with 7 to 21 C atoms and n is typically 2-100.

In one of the preferred form of the present invention, one or more of the compositions A, B and C and more preferably Composition C comprises at least one cationic polymer as a conditioning agent. Suitable cationic polymers are those of best known with their CTFA category name Polyquaternium. Typical examples of those are Polyquaternium 1, Polyquaternium 2, Polyquaternium 4, Polyquaternium 5, Polyquaternium 6, Polyquaternium 7, Polyquaternium 8, Polyquaternium 9, Polyquaternium 10, Polyquaternium 11, Polyquaternium 12, Polyquaternium 13, Polyquaternium 14, Polyquaternium 15, Polyquaternium 16, Polyquaternium 17, Polyquaternium 18, Polyquaternium 19, Polyquaternium 20, Polyquaternium 22, Polyquaternium 24, Polyquaternium 27, Polyquaternium 28, Polyquaternium 29, Polyquaternium 30, Polyquaternium 31, Polyquaternium 32, Polyquaternium 33, Polyquaternium 34, Polyquaternium 35 and Polyquaternium 36, Polyquaternium-37, Polyquaternium 39, Polyquaternium 42, Polyquaternium 43, Polyquaternium 44, Polyquaternium 45, Polyquaternium 46, Polyquaternium 47, Polyquaternium 48, Polyquaternium-49, Polyquaternium 50, Polyquaternium 51, Polyquaternium 52, Polyquaternium 53, Polyquaternium 54, Polyquaternium 55, Polyquaternium 56, Polyquaternium 57, Polyquaternium 58, Polyquaternium 59, Polyquaternium 60, Polyquaternium 61, Polyquaternium 62, Polyquaternium 63, Polyquaternium 64, Polyquaternium 65, Polyquaternium 66, Polyquaternium 67, Polyquaternium 68, Polyquaternium 69, Polyquaternium-70, Polyquaternium 71, Polyquaternium 72, Polyquaternium 73, Polyquaternium 74, Polyquaternium 75, Polyquaternium 76, Polyquaternium 77, Polyquaternium 78, Polyquaternium-79, Polyquaternium 80, Polyquaternium 81, Polyquaternium 82, Polyquaternium 83, Polyquaternium 84, Polyquaternium 85, and Polyquaternium 86.

It has further been found out that especially those of cationic cellulose type polymers known as Polymer JR type from Amerchol such as Polyquaternium 10 or cationic galactomannans such as cationic guar gum known with trade name Jaguar from Rhône-Poulenc which are chemically for example Guar hydroxypropyl trimonium chloride and cationic tara gum an its derivatives known with INCI name *Caesalpinia spinosa* hydroxypropyltrimonium chloride, are preferred ones.

The most preferred cationic polymers are those of cationic cellulose derivatives, cationic guar gum derivatives, cationic Caesalpinia spinosa gum derivatives, polyquaternium 6, polyquaternium 7, polyquaternium 67 and polyquaternium 70.

The cationic polymers also include the quaternized products of graft polymers from organopolysiloxanes and polyethyl oxazolines described in EP-A 524 612 and EP-A 640 643.

Compositions comprise cationic polymer at a concentration of 0.01 to 5%, preferably 0.02 to 4%, more preferably 0.05 to 3% and most preferably 0.1 to 2.5% by weight calculated to total of each composition.

Compositions A, B and C may further comprise at least one ubiquinone of the formula

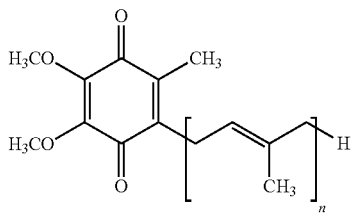

where n is a number between 1 and 10 at a concentration of 0.0001 to 1%, preferably from 0.0002 to 0.75%, more preferably from 0.0002 to 0.5% and most preferably from 0.0005 to 0.5% by weight, calculated to total of each composition.

The compositions comprise ubiquinone which is preferably selected from the ones where n is a number between 6 and 10 and more preferably it is ubiquinone 50 where n is 10, also known as Coenzyme Q10.

One or more of the compositions A, B and C can comprise further ceramide type of compound with the general formula

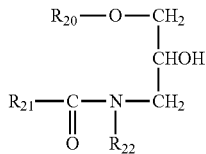

where $R_{20}$ and $R_{21}$ are independent from each other alkyl- or alkenyl group with 10 to 22 carbon atoms, $R_{22}$ is alkyl or hydroxyl alkyl with 1 to 4 carbon atoms group and n is a number between 1 to 6, preferably 2 or 3. Preferred compound according to the above chemical structure is cetyl-PG-hydroxyethylpalmitamide.

One or more of the composition A, B and C preferably comprises organic solvents. Non-limiting examples of such organic solvents are benzyloxy ethanol, benzyl alcohol, phenoxy ethanol, phenoxy isopropanol, methyl phenoxy ethanol, benzyl glycerol, N-benzyl formide, N-methylpyrrolidone, N-ethyl pyrrolidone, cinnamyl alcohol, phenethyl alcohol, p-methyl benzyl alcohol, butyl cellosolve, methyl carbitol, ethyl carbitol, propyl carbitol, butyl carbitol, diethyleneglycol, diethyl ether and dipropyleneglycol diethyl ether. Typically the concentration of those solvents can be in the range from 0.1% to 20%, preferably 0.2-15%, more preferably 0.25-10%, by weight calculated to the total of each composition.

The three compositions of the present invention may comprise any additional compounds customarily found in these types of compositions such as antioxidants, chelating agents, fragrance, any preservatives.

Following examples are to illustrate the invention but not to limit.

Example 1

| Composition A | |
|---|---|
| | by weight |
| Sodium lauroyl glutamate | 1.0 |
| Argan oil | 0.2 |
| Basic red 51 | 1.0 |
| Monoethanolamine | 4.0 |
| Ammonia (25%) | 5.0 |
| Water | q.s. to 100 |

The above composition was prepared by dissolving and mixing the given components in water. The pH of the composition was 9.8.

| Composition B | |
|---|---|
| Hydrogen peroxide | 9.0 |
| Phosphoric acid | q.s. to pH 3.0 |
| Water | q.s. to 100 |

| Composition C | |
|---|---|
| | % by weight |
| Sodium lauroyl glutamate | 4.0 |
| Decyl glucoside | 5.0 |
| Cocamidopropyl betaine | 5.0 |
| Polyquaternium-6 | 0.5 |
| PEG-90 Glyceryl isosterate | 1.5 |
| Citric acid/sodium hydroxide | q.s. to pH 5.5 |
| Preservative, fragrance | q.s |
| Water | to 100 |

Human hair was coloured by application of a composition prepared by mixing equal amounts of the compositions A and B and processing for 30 min at ambient temperature and hair was rinsed off with water and subsequently hair was washed with composition C. It was observed that hair was coloured homogeneously into an intensive red colour and hair so coloured was well cared in terms combability, shine and softness. After subsequent washes it was observed that the colour intensity remained.

Example 2

| Composition A | |
|---|---|
| | by weight |
| Sodium cocoyl glutamate | 1.0 |
| Argan oil | 0.2 |
| p-phenylendiamine | 0.5 |
| Resorcinol | 0.5 |
| Monoethanolamine | 4.0 |
| Ammonia (25%) | 5.0 |
| Water | q.s. to 100 |

Composition B

| | |
|---|---|
| Hydrogen peroxide | 6.0 |
| Sodium lauroyl gluatamate | 0.5 |
| Phosphoric acid | q.s. to pH 3.0 |
| Water | q.s. to 100 |

Composition C

| | % by weight |
|---|---|
| Sodium lauroyl glutamate | 4.0 |
| Decyl glucoside | 5.0 |
| Cocoyl betaine | 5.0 |
| Polyquaternium-10 | 0.8 |
| PEG-90 Glyceryl isosterate | 1.5 |
| Citric acid/sodium hydroxide | q.s. to pH 5.0 |
| Preservative, fragrance | q.s |
| Water | to 100 |

Human hair was coloured by application of a composition prepared by mixing equal amounts of the compositions A and B and processing for 30 min at ambient temperature and hair was rinsed off with water and subsequently hair was washed with composition C. It was observed that hair was coloured homogeneously and hair so coloured was well cared in terms combability, shine and softness. After subsequent washes it was observed that the colour intensity remained.

The invention claimed is:

1. Process for treating hair comprising the steps wherein hair is dyed with a composition comprising one or more hair dye and at least one oxidizing agent wherein the composition is obtained by mixing two compositions prior to application onto hair wherein a first Composition A comprises one or more hair dye and a second Composition B comprises at least one oxidizing agent, and in a further step hair is treated with a third Composition C comprising at least one surfactant other than amino acid surfactant, with the condition that at least two of the Compositions A, B and C comprise at least one amino acid surfactant and composition C is substantially free of sulphate surfactant.

2. The process according to claim 1 wherein Composition A comprises one or more hair direct dye selected from cationic, anionic and neutral nitro dyes.

3. Process according to claim 1 wherein Composition A comprises one or more oxidative dye precursor.

4. Process according to claim 1 wherein at least one amino acid surfactant is selected from surfactants according to general structure

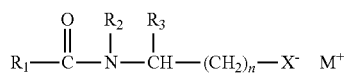

wherein $R_1$ is a saturated or unsaturated, straight or branched alkyl chain with 7 to 17 C atoms, $R_2$ is H or a methyl, $R_3$ is H, $COO^-M^+$, $CH_2COO^-M$ or COOH, n is 0 to 2, X is $COO^-$ and M is independent from each other H, sodium, potassium or ammonium.

5. Process according to claim 4 wherein at least one amino acid surfactant is selected from glutamate, alanin or alaninate, sarcosinate, aspartate surfactants, and mixtures thereof, glutamate and sarcosinate surfactants.

6. Process according to claim 1 wherein Composition B comprises hydrogen peroxide.

7. Process according to claim 1 wherein composition A comprises at least one alkalizing agent.

8. Process according to claim 1 wherein composition C is a cleansing composition.

9. Process according to claim 8 wherein composition C comprises one or more surfactants selected from anionic, non-ionic and amphoteric surfactants other than amino acid surfactant and it is free of sulphate surfactants.

10. Process according to claim 8 wherein composition C comprises surfactants at a total concentration in the range of 5 to 25% by weight, calculated to the total of composition C.

11. Process according to claim 1 wherein one or more of the compositions A, B and C comprises at least one natural oil.

12. Process according to claim 1 wherein one or more of the compositions A, B and C comprises at least one fatty alcohol.

13. Process according to claim 1 wherein one or more of the compositions A, B and C comprises at least one cationic surfactant according to the formula,

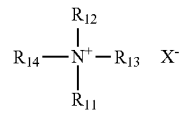

where $R_{12}$ is a saturated or unsaturated, branched or non-branched alkyl chain with 8-22 C atoms or

where $R_{15}$ is saturated or unsaturated, branched or non-branched alkyl chain with 7-21 C atoms and n has typical value of 1-4 or

where $R_{16}$ is saturated or unsaturated, branched or non-branched alkyl chain with 7-21 C atoms and n has typical value of 1-4, and $R_{11}$ is unsaturated or saturated, branched or non-branched alkyl chain with 1-22 C atoms or

or

where $R_{15}$, $R_{16}$ and n are same as above.

$R_{13}$ and $R_{14}$ are lower alkyl chain with 1 to 4 Carbon atoms, and X is chloride, bromide or methosulfate.

14. Kit for treating hair comprising at least three compositions wherein a first Composition A comprises one or more hair dye, a second Composition B comprises at least one oxidizing agent and a third Composition C comprises at least one surfactant other than amino acid surfactant, with the condition that at least 2 of the Compositions A, B and C, comprise at least one amino acid surfactant and composition C is substantially free of sulphate surfactant.

* * * * *